Dec. 29, 1953
Plant Pat. 1,237
F. SPANBAUER
ROSE PLANT
Filed Dec. 29, 1952
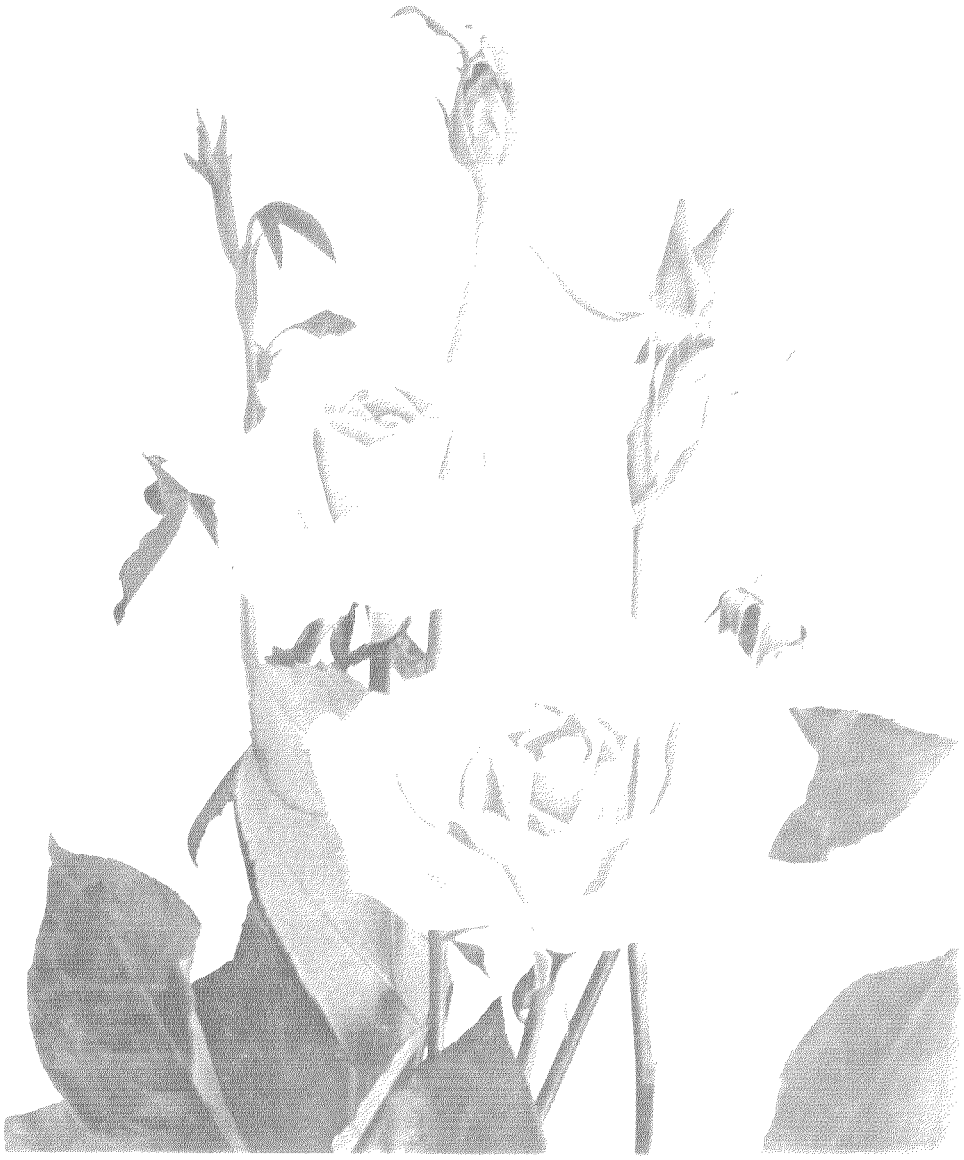
Inventor
Frank Spanbauer
By: Robert Robb
Attorney Patented Dec. 29, 1953 Plant Pat. 1,237

UNITED STATES PATENT OFFICE 1,237

ROSE PLANT

Frank Spanbauer, Decatur, Ill.

Application December 29, 1952, Serial No. 328,541

1 Claim. (Cl. 47—61)

The present invention relates to a new and distinct variety of rose plant of the hybrid tea class, which originated as a sport of the variety "Better Times" (Plant Patent No. 23). The sport was found by me at Decatur, Illinois, among cultivated plants of "Better Times" which I was growing in my greenhouses. While in the act of cutting flowers from some of the "Better Times" plants in my greenhouses, my attention was attracted to a light pastel pink bloom which I found had sprung off one side of a "Better Times" plant, and I thereupon carefully preserved the sport and promptly took steps to asexually reproduce the same in order to develop it and ascertain whether the new color characteristic of the bloom was permanently established and transmissible by asexual reproduction.

In the course of asexually reproducing my new variety by cuttings, grafting and budding, at Decatur, Illinois, I found that the new variety was not only distinguished from "Better Times" by the light pastel pink color of its blooms, but I also found that it had other desirable characteristics which distinguish it from its parent, as well as from all other varieties of its class, the most outstanding distinguishing features being as follows:

(1) The plants of the new variety are upright and bushy in form, and are endowed with a very vigorous freedom of growth;

(2) The foliage is normal green in color but somewhat more leathery than the foliage of "Better Times";

(3) The buds are long-pointed in form and relatively large in size, while the open flowers are full, large and almost flat-topped, with more petals than those of "Better Times," free from "bullheading," and borne on stronger, slightly longer and larger stems than those of "Better Times";

(4) The general color tonality of the flowers of the new variety is best described as Neyron Pink, as distinguished from the cerise color of "Better Times," and the color of the flowers of my new variety is more uniform and holds much better and longer without any bluing of the petals, as compared with "Better Times," with excellent lasting quality of the blooms; and (5) Under the same cultural conditions in both the greenhouse and outdoors, my new variety produces appreciably more blooms than its parent "Better Times," or other pink varieties heretofore known, thereby making my new variety an excellent one for commercial production.

Asexual reproduction of my new variety by cuttings, grafting and budding, as performed at Decatur, Illinois, shows that the foregoing characteristics and distinctions come true to form and are established and transmitted through succeeding propagations.

The accompanying drawing shows specimens of the flowers, foliage and stems of my new variety in different stages of development.

The following is a detailed description of my new variety, with color terminology in accordance with the Horticultural Color Chart issued by the British Color Council, except where general color terms of ordinary dictionary significance are obvious:

Type: Hardy; greenhouse and outdoor; sport; for cut flowers and for garden decoration.
Class: Hybrid tea.
Breeding: Sport of "Better Times."
Propagation: Holds its distinguishing characteristics through succeeding propagations by cuttings, grafting and budding.

*Flower*

Locality where grown and observed: Decatur, Illinois.
Continuity: Continuous.
Fragrance: Slight; very weak citrus scent.
Flowers borne: Singly; on strong, long stems.
Quantity of bloom: Profuse both outdoors and in greenhouse.
Bud:
*Peduncle.*—Long; heavy; erect; stiff; entirely smooth; no hairs. Color.—Light green.
*Before calyx breaks.* — Size — medium. Form—pointed; with a conspicuous neck; with foliaceous appendages on the surface of the bud; with slender, bristle-like foliaceous parts extending beyond the tip of the bud equal to ¼ of its length. Color—Spinach Green, Plate 960–1.
*As calyx breaks.*—Color—Claret Rose, Plate 21–2.
*As first petal opens.*—Size—medium-large. Form — long-pointed. Color — outside: Neyron Rose, Plate 623–2; inside: Neyron Rose, Plate 623–1.
*Opening.*—Opens up well; is not retarded from opening by cold, hot, wet or dry weather.
Bloom: Size, when fully open—large; from 4 inches to 4½ inches.
*Petalage.*—Double (more petals, but the stamens not hidden); from 32 to 34 petals; arranged regularly.
*Form.*—Flat-open; full center at first; remaining flat-open; petals being at first tightly rolled inward; becoming later at maturity loosely rolled outward and almost flat.

Petals: Thick; leathery; with both inside and outside satiny.

*Shape.*—Outside—round to almost orbicular. Intermediate—round. Inside—round.

*Color.*—Color remains practically the same under ordinary greenhouse conditions.

This description of a newly opened flower was made from a rose grown in a greenhouse in the month of November, at Decatur, Illinois:

*Color.*—Outside petal—outside surface: Neyron Rose, Plate 623–1; inside surface: Neyron Rose, Plate 623–1. Intermediate petal—outside surface; Neyron Rose, Plate 623–1; inside surface; Neyron Rose, Plate 623–1. Inner petal—outside surface: Neyron Rose, Plate 623–1; inside surface: Neyron Rose, Plate 623–1.

This description was made from a rose that was open for three days in a greenhouse in the month of November, at Decatur, Illinois:

*Color.*—Outside petal—outside surface: Neyron Rose, Plate 623–2; inside surface: Neyron Rose, Plate 623–2. Inside petal—outside surface: Neyron Rose, Plate 623–1; inside surface: Neyron Rose, Plate 623–1.

*General color effect.*—Newly opened flower—Neyron Rose, Plate 623–1. Three days open—Neyron Rose, Plate 623–2.

*Behavior.*—Drop off cleanly; never blues or purples; remains uniform color under glass.

*Flower longevity.*—On bush in garden—5 days or more from June to November. Cut roses grown outdoors and kept at living room temperatures—6 days from June to November. Cut roses grown in greenhouse and kept at living room temperatures—6 days in any month.

*Reproductive organs*

Stamens: Medium number; arranged irregularly about pistils. Color—Cadmium Orange, Plate 8–2.

Filaments: Medium-length; most with anthers. Color—yellow.

Anthers: Large; open at various times. Color—yellow.

Pollen: Moderate abundance. Color—gold.

Pistils: Medium number.

Styles: Uneven; medium-length; medium caliper; bunched.

Stigma: Color—whitish yellow.

Ovaries: All enclosed in calyx.

Hips: Globular; smooth; walls thick and dry. Color—yellow.

Sepals: Falling soon; moderate length; curled.

Color—Spinach Green, Plate 960–1.

Seeds: Very few; medium size.

*Plant*

Foliage:

*Leaves.*—Compound of 5 leaflets; moderately abundant; medium-large; leathery.

*Leaflets.*—Ovate in shape; with acute apex; round base; simply serrate.

*Color.* — Mature — upper surface: normal dark green; under surface: normal grey-green. Young—upper surface: moderately light red; under surface: light greenish-red.

*Rachis (the supporting stem of the compound leaf).*—Heavy. Upper side—smooth. Under side—sparsely prickly.

*Stipules.* — Medium-long; medium - width; with medium-long points turning out at an angle of less than 45°.

*Disease resistance.*—Resistant to mildew and blackspot, as determined by comparison with other varieties grown under the same cultural conditions at Decatur, Illinois.

Growth:

*Habit.*—Bushy; upright; branched.

*Growth.*—Free and vigorous.

*Canes.*—Medium-heavy.

*Main stems.* — Color — bright green. Thorns—few; medium-length; slightly curved downward; with long, narrow base. Prickles—none. Hairs—none.

*Branches.*—Color—bright green. Thorns—few; medium-length; slightly curved downward; with long, narrow base. Prickles—none. Hairs—none.

*New shoots.*—Color—bright red. Thorns—few; short; slightly curved downward; with long, narrow base. Prickles—none. Hairs—none.

I claim:

A new and distinct variety of rose plant of the hybrid tea class, substantially as herein shown and described, characterized particularly as to novelty by its upright and bushy habit of growth, by its relatively leathery foliage, by its relatively large and long-pointed buds, by its full-petaled flowers of Neyron Pink general color tonality, by the uniformity of the color of its blooms and their good-keeping and long-lasting quality with complete absence of bluing of the petals, by its habit of bearing flowers on relatively strong, long and large stems, by its freedom from "bullheading" of the flowers, and by its freedom and profusion of blooms, with attending superior production for cut-flower purposes.

FRANK SPANBAUER.

No references cited